(12) United States Patent
Garreau et al.

(10) Patent No.: US 8,093,912 B2
(45) Date of Patent: Jan. 10, 2012

(54) MICROWAVE DEVICE FOR CONTROLLING MATERIAL

(75) Inventors: Philippe Garreau, Mennecy (FR); Jérôme Drean, Paris (FR); Luc Duchesne, Angervilliers (FR); Arnaud Gandois, Breuillet (FR); Ludovic Durand, Leuville sur Orge (FR); Virginie Tessier, Le Plessis Robinson (FR); Per Iversen, Marietta, GA (US); Nicolas Robic, Languidic (FR)

(73) Assignee: Ste d'Applications Technologiques de l'Imagerie Micro-Onde, Villebon sur Yvette (FR)

( * ) Notice: Subject to any disclaimer, the term of this patent is extended or adjusted under 35 U.S.C. 154(b) by 446 days.

(21) Appl. No.: 12/442,909

(22) PCT Filed: Sep. 25, 2007

(86) PCT No.: PCT/EP2007/060150
§ 371 (c)(1),
(2), (4) Date: Mar. 25, 2009

(87) PCT Pub. No.: WO2008/037705
PCT Pub. Date: Apr. 3, 2008

(65) Prior Publication Data
US 2010/0005891 A1 Jan. 14, 2010

(30) Foreign Application Priority Data
Sep. 25, 2006 (FR) ...................................... 06 08398

(51) Int. Cl.
*G01R 27/04* (2006.01)
*A61B 5/05* (2006.01)
*G06K 9/00* (2006.01)

(52) U.S. Cl. ........ 324/639; 324/637; 600/425; 382/131; 382/149

(58) Field of Classification Search ................... 324/637, 324/629, 600; 382/128, 131, 149; 600/407, 600/425
See application file for complete search history.

(56) References Cited

U.S. PATENT DOCUMENTS
5,128,621 A * 7/1992 Berthaud et al. .............. 324/639
(Continued)

FOREIGN PATENT DOCUMENTS
EP 0 069 628 1/1983
(Continued)

OTHER PUBLICATIONS

PH. Garreau et al., Probe Array Concepts for Fast Testing of Large Radiating Structures, 26th Annual Antenna Measurement Technologies Associations, Oct. 2004, XP002429703.

*Primary Examiner* — Hoai-An D Nguyen
(74) *Attorney, Agent, or Firm* — Pauley Petersen & Erickson

(57) ABSTRACT

The invention relates to a device for controlling a material, the device including at least one transmitter for transmitting an electromagnetic signal at a carrier frequency Fp to illuminate the material and one receiver for receiving the electromagnetic signal, wherein the device further includes a first modulator for modulating the electromagnetic signal at a frequency Fm1, the first modulator being arranged, on the signal path, between the transmitter and the material in order to spatially sample the emitted electromagnetic signal; second modulator for modulating the electromagnetic signal at a frequency Fm2, the second modulator being arranged, on the signal path, between the material and the electromagnetic signal receiver in order to spatially sample the electromagnetic signal passed through the material.

15 Claims, 4 Drawing Sheets

U.S. PATENT DOCUMENTS

| | | | |
|---|---|---|---|
| 5,619,143 A | 4/1997 | Stevens et al. | |
| 5,715,819 A * | 2/1998 | Svenson et al. | 600/425 |
| 5,807,263 A * | 9/1998 | Chance | 600/476 |
| 5,841,288 A | 11/1998 | Meaney et al. | |
| 2008/0296514 A1* | 12/2008 | Metzger et al. | 250/492.1 |
| 2011/0040176 A1* | 2/2011 | Razansky et al. | 600/425 |

FOREIGN PATENT DOCUMENTS

| | | |
|---|---|---|
| EP | 0 940 672 A | 9/1999 |
| FR | 2 614 419 A1 | 10/1988 |
| WO | WO 95/32665 A | 12/1995 |

* cited by examiner

MICROWAVE DEVICE FOR CONTROLLING MATERIAL

FIELD OF THE INVENTION

The present invention relates to a device for controlling a material. The present invention also relates to a method using said device.

TECHNOLOGICAL BACKGROUND

The device according to the invention can be used for different applications.

In particular, the device according to the invention enables controls of materials that are not entirely composed of metal, such as wood, paper, rock or glass wool, glass, plastics, agri-food compatible material, or radiating elements, etc.

For such types of materials, the device can especially enable measurement of material physical properties (density, moisture) or even detection of defects of the controlled material (cavities, inclusions, etc.).

Controlling materials on industrial production lines requires use of devices that are rapid and most frequently non-invasive. Such non-invasive devices are known, such as X-ray, gamma, and infrared or ultrasound devices, for example, each of these devices having its own specific applications.

To improve the performance of these devices, it has been suggested to combine them so as to at least be able to obtain the advantages of each device taken independently.

However, for applications to non-metallic materials, even though use of devices based specifically on electromagnetic waves provides definite advantages (in particular substantial penetration of electromagnetic waves into the interior of non-metallic materials), current technology remains limited with regard to industrial applications.

Indeed, such industrial applications require real-time measurements considering speed rate at which the material to be inspected progresses along the production line and considering the necessity to control large sections of the materials.

The purpose of the invention is to remedy the limitations mentioned above.

More precisely, a first purpose of the present invention is providing a device capable of controlling a material that is not entirely composed of metal.

Another purpose of the invention is providing a device that can conduct a real-time control of material.

Yet another purpose of the invention is enabling control over large portions of the materials.

Still another purpose of the invention is providing a modular device that is easily adaptable to all types of production lines and easily installed.

PRESENTATION OF THE INVENTION

To this end, the object of the invention is to provide a device for controlling a material, said device comprising at least means for transmitting an electromagnetic signal at a carrier frequency Fp to illuminate the material and means for receiving the electromagnetic signal, characterized in that said device further comprises first means for modulating the electromagnetic signal at a frequency Fm1, said modulation means being arranged, on the signal path, between the transmission means and the material in order to spatially sample the emitted electromagnetic signal; second means for modulating the electromagnetic signal at a frequency Fm2, said modulation means being arranged, on the signal path, between the material and the electromagnetic signal reception means in order to spatially sample the electromagnetic signal passed through the material.

BRIEF DESCRIPTION OF THE DRAWINGS

The invention will be easier to understand, and other objectives, aims, and advantages will become clear on reading the following description, provided for non-limiting purposes, with reference to the appended drawings, in which.

DETAILED DESCRIPTION OF THE INVENTION

1. Device for Controlling a Material in Transmission Mode

Figure 1:
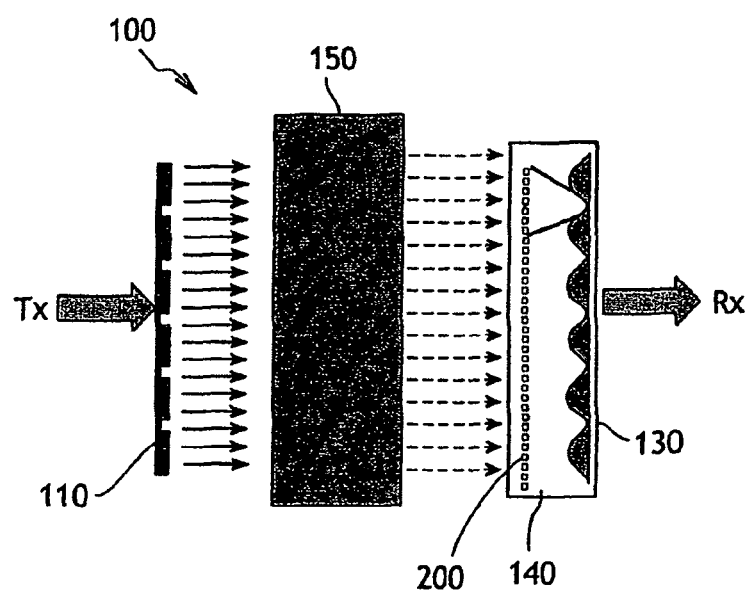
FIG. 1 shows a schematic view of a device for controlling a material in transmission mode.
Figure 2:
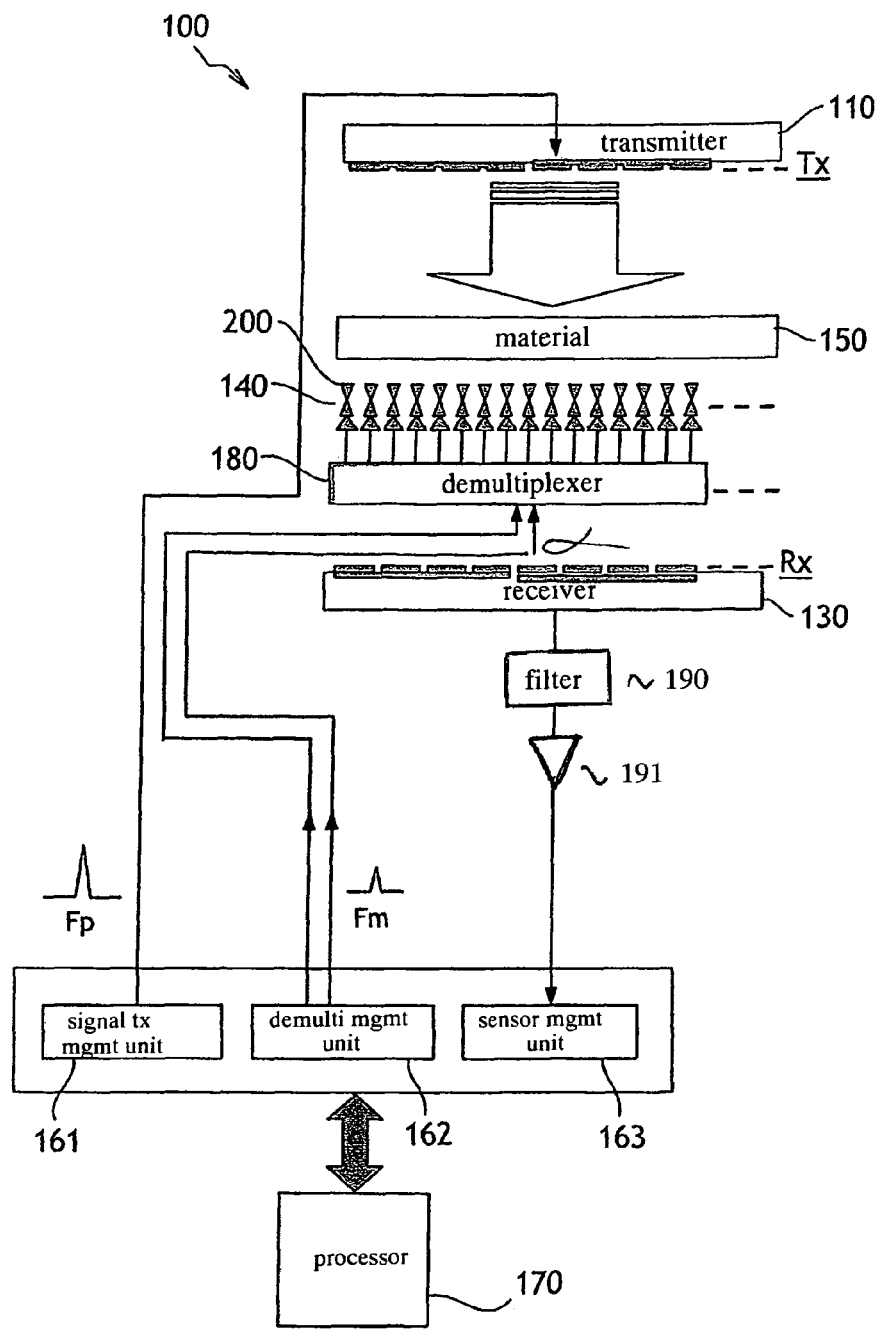
FIG. 2 shows a block diagram of a device for controlling a material according to the invention.

FIGS. 1 and 2 feature a device 100 for controlling a material 150 in a transmission configuration.

The control device 100 appears in the form of:

transmission means 110 of an electromagnetic signal at a carrier frequency Fp for illuminating the material 150 to be controlled;

modulation means 140 at a frequency Fm2 of the electromagnetic signal received from the material 150;

reception means 130 of the electromagnetic signals created by the modulation.

Modulation means 140 are arranged, on the signal path, between the material 150 and reception means 130 of the electromagnetic signals created by the modulation.

Transmission means 110, on one hand, and modulation 140 and reception means, on the other hand, are arranged on either side of the material 150 under examination such that the modulation means 140 receive the transmitted signal after it has passed through the material 150.

a. Transmission Means

Transmission means 110 comprise an array of adjacent transmission antennas intended to transmit the electromagnetic signal at the carrier frequency Fp. The signal, more precisely, is an electromagnetic plane wave. The frequency Fp falls within the field of microwave frequencies.

The antennas are preferably patch antennas.

b. Modulation Means

Modulation means 140 include an array of sensors 200 arranged facing the material 150 and aligned in a common plane perpendicular to propagation direction of the signal transmitted by transmission means 110.

The role of modulation means is to locally disturb the electromagnetic field at the modulation frequency F2 in order to spatially sample the electromagnetic signals passed through the material 150 into as many independent signals as there are sensors 200.

The sensors 200 integrating the modulation elements for the spatial separation will be described in greater detail in association with FIGS. 4 and 5.

Furthermore, an alternative embodiment of the present invention suggests modulation means that produce the following modulation frequencies: Fm2, Fm2-1, Fm2-2 . . . Fm2-i, with "i" corresponding to the $n^{th}$ sensor.

c. Reception Means

Reception means 130 moreover include an array of aligned reception antennas preferably of the same type or even identical to the antennas of the transmission array.

The array of reception antennas is positioned behind the array of spatial modulation sensors 200.

Said array of reception antennas is intended to collect the signals at the carrier frequency and the signals at the modulated frequencies Fp±Fm resulting from the modulation.

In one variation of the embodiment of reception means 130, the array of reception antennas and the array of spatial modulation sensors 200 can be found as an array of independent elements each including an integrated reception antenna and an integrated spatial modulation sensor.

d. Other Elements of the Control Device

As can be seen in FIG. 2, the device also includes means 180 for demultiplexing the signal modulated at the frequency Fm2. Said demultiplexing means 180 serve to address the different sensors 200, that is to say they enable reception means 130 to distinguish the origin of the different signals resulting from the sensors 200.

Said demultiplexing means can be either temporal or spatial demultiplexing means.

In the case of temporal demultiplexing, the distinction is achieved by distributing sequentially the modulating signal toward the different sensors 200.

In the case of spatial demultiplexing, the distinction is achieved by attributing a different modulation frequency Fm or a set of orthogonal modulations to each sensor 200 of the array simultaneously.

The device further includes filtering means 190 and amplification means 191 of the signals at the carrier frequency Fp and at modulated frequencies Fp±Fm received by reception means 130.

More precisely, filtering means 190 include a band pass filter in which the cut off frequency and the bandwidth are adapted to eliminate the carrier frequency Fp prior to amplification of the modulated signals.

The effective dynamic range of the functioning of a sensor collecting the rays having passed through the material 150 is thus updated based on the signals modulated at frequencies Fp±Fm whose levels customarily range from 60-80 dB below that of the selected carrier frequency Fp.

Filtering means 190 allow for the receiver 130 not to be saturated by the signal at the carrier frequency Fp, thereby making it possible to obtain far better dynamics of the device.

In the case of a device of multiple carrier frequencies, it is possible to use filters that are centered on each of the carrier frequencies and that move along the frequency bands such as, for example, Yttrium Iron Garnet YIG filters.

Furthermore, amplification means 191 include a low noise amplifier intended to receive the filtered signals and to amplify them prior to their being collected by the receiver 130.

Finally, the device has a processor 170 that communicates with specific units 161, 162, and 163 which are respectively intended to manage transmission of the signal at the level of transmission means 110, demultiplexing means, and the receiver 130 connected to the reception means in order to measure the real and imaginary parts of the modulated electromagnetic signals.

The processor 170 likewise includes means for treating the real and imaginary signals from the receiver 130 in order to improve disturbance detection of the electromagnetic signal transmitted by transmission means 110.

The processor 170 furthermore includes display means for the post-treatment display of an image of the controlled material 150, said image being created on the basis of the signals resulting from the modulation.

e. Operating Principle of the Control Device

With such means, it is possible to use a process in which an electromagnetic signal is transmitted at a frequency Fp in order to illuminate the material 150 to be controlled.

Furthermore, once the electromagnetic signal has been transmitted by transmission means 110, it propagates across the material 150 to be controlled.

The slightest inhomogeneity of the material 150 or a difference in density, moisture or temperature thereof can bring about a change in the behavior of the electromagnetic field propagated in the material 150.

Similarly, the presence of defects, due to their dielectric or magnetic properties, which are different from those of the material 150, results in a disturbance of the electromagnetic signal propagated in the material 150 at the location of the defect.

The signal thus modified is received by the sensors 200 of the array of modulation means 140.

Thereafter, in each of its sensors 200, the electromagnetic signal issued from the material 150 is modulated at a modulation frequency Fm2. The modulated signals issued from each sensor 200 are subsequently received by the antennas of reception means 130.

In this manner, it is possible to recognize, subsequent to reception at the level of reception means 130 of the signals that have already been modulated, which sensor(s) 200 have detected a disturbed signal. This particular sensor 200 will correspond with a localized zone of the material 150.

These signals modulated and received by reception means 130 are then filtered, amplified, and treated in order to obtain an image of the material 150 to be controlled.

The disturbance of an electromagnetic signal caused by the presence of defects in a zone of the material 150 will be visible on the image atone or more specific sensors 200, thereby making it possible for the defect to be located.

Similarly, the inhomogeneity or the difference in density, moisture or temperature in the material 150 will be detected by the device.

In an alternative embodiment of FIG. 1, the radiating parts of the device being reciprocal, provisions have moreover been made for transmissions to be transmitted by the antennas of the reception means 130 and for receptions to be received by the antennas of the transmission means 110.

f. Double Modulation Inspection Device

It has been allowed for to add to the device of FIG. 1 means to modulate the signal transmitted by transmission means 100 at the modulation frequency Fm1.

This modulation frequency Fm1 can be identical to or different from the modulation frequency of the electromagnetic signal received by the material 150.

Figure 4:
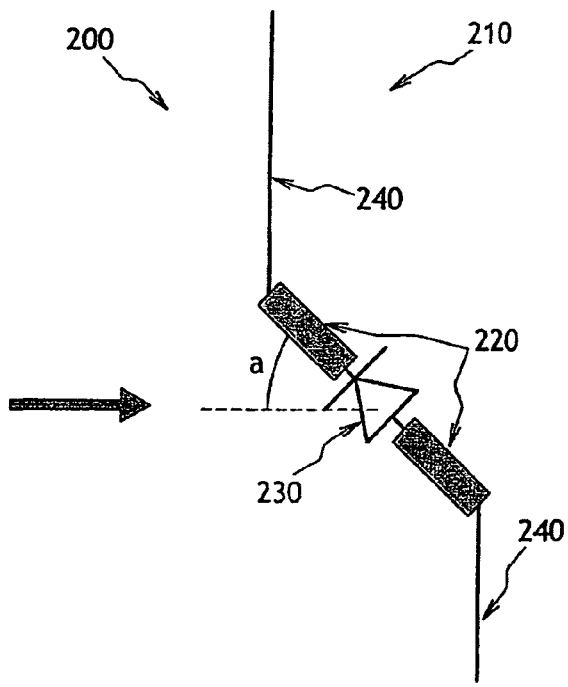
FIG. 4 shows a schematic view of a sensor having a modulation element.
Figure 5:
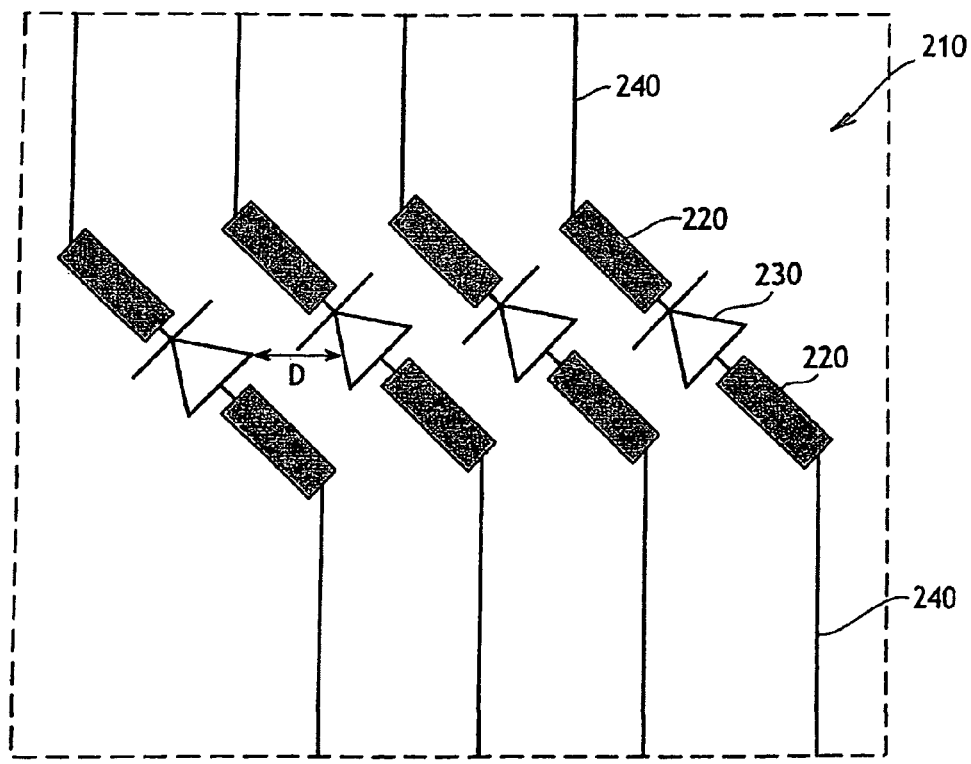
FIG. 5 shows a diagram of an array of sensors having the modulation elements according to FIG. 4.

These means are similar to modulation means 140 hereinbefore mentioned and described in relation to FIGS. 4 and 5.

Moreover, a variant of the embodiment of the present invention proposes modulation means that present the following modulations: Fm1, Fm1-1, Fm1-2 . . . Fm1-i, with "i" corresponding to the $n^{th}$ sensor.

The modulation means are arranged on the signal path between transmission means 110 and the material to be analyzed 150.

They spatially sample the electromagnetic signal transmitted by transmission means 110 into as many signals as there are sensors in the array of modulation means.

A double modulation of the electromagnetic signal at the carrier frequency Fp is thus obtained.

For each transmission point of the electromagnetic signal, the signal having passed through the material is received by the collection of sensors 200 of the array of modulation means 140.

The signal collected on the sensor thus corresponds to different electromagnetic signal paths having passed through the material 150.

The collection of electromagnetic signal paths passing through the material 150 between all sensors of the two arrays is thus measured point-to-point.

This makes it possible to achieve multistatic tomographic imagery in the analyzed material 150 and to obtain reconstructed images of high quality.

2. Device for Controlling a Material in Reflective Mode

Figure 3:
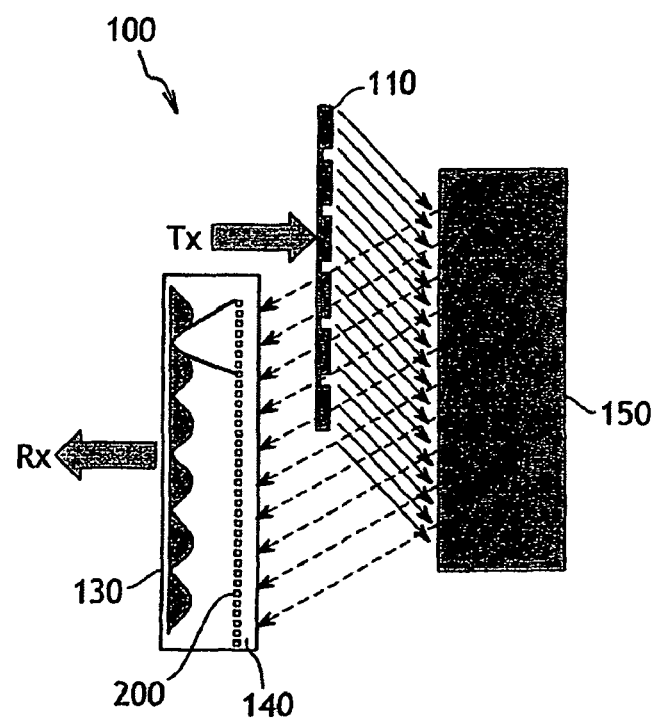
FIG. 3 shows a schematic view of a device for controlling a material according to the invention in reflective mode.

FIG. 3 shows a control device of material 150 in reflective mode. The means and theory of operation are the same as that of the control device in the transmission mode.

The difference rests primarily in the arrangement of transmission means 110, modulation means 140, and reception means 130.

In the reflection mode, transmission means, on one hand, and modulation 140 and reception 130 means, on the other hand, are arranged on the same side of the material 150 to be controlled such that modulation means 140 receive the signal reflected by the material 150.

This device offers the advantage of operating in double transmission since in this mode, the electromagnetic signal at the carrier frequency passes twice through the material 150 being examined. This type of device is advantageous in cases where one side of the material 150 to be measured cannot be accessed or when the material 150 to be tested has a metal surface.

One embodiment allows for the placement of a metal plate behind the material 150 under examination on the side opposite transmission means 110, modulation means 140, and reception means 130 in order to improve the reflection.

3. Array of Sensors

The sensor 200 of the spatial modulation depicted in FIG. 4 consists of four main elements, that is to say a collection of radiating wires 220, a nonlinear electronic component 230, feed wires 240, and a substrate 210.

The principle of operation of a sensor 200 is described for the sensors 200 of modulation means 140 positioned on the signal path between the material 150 and reception means 130. The description is as follows.

The radiating wires 220 of the sensor 200 will pick up the electromagnetic signal at the carrier frequency Fp passed through the material 150.

The wires 220 are moreover charged by the nonlinear electronic component 230 that is itself polarized with the assistance of a signal at a modulation frequency Fm2.

They thus generate a signal modulated at the frequency Fp±Fm2, a signal that will be received by reception means 130.

More precisely, each sensor 200 includes two radiating wires 220 each connected on either side of the nonlinear electronic component 230.

The nonlinear electronic component 230 is preferably an electric or photoelectric diode.

It can also likewise be a nonlinear electronic component sensitive to temperatures such as a thermistor.

The effectiveness of the modulation of the sensor 200 is directly linked to the contrast between the on state and the off state of the diode.

The two radiating wires 220 are preferably in the shape of a rectangular segment. In one variant, other shapes are possible for the radiating wires 220.

The size of the wires 220 is preferably small compared to the wavelength.

It should be noted that the more the surface of the wires 220 increases, the greater the amplitude of the electromagnetic signal modulated at the frequency Fp±Fm2.

Furthermore, the wires 220 are positioned in an angular configuration determined with respect to the direction of the polarization of the array of antennas of transmission means 110. The angle $\alpha$ formed between the longitudinal direction of the wires and the direction of polarization of the array of antennas can be between 0° and 180°.

The wires 220 are preferably positioned at $\alpha=45°$ with respect to the direction of polarization of the array of antennas of transmission means 110.

This provides the advantage of reducing the spacing between the different sensors 200 of an array, which results in increasing the density of the sensors 200 and thereby improving the spatial resolution of the device 100 as will be described hereinafter in relation to FIG. 5.

Thus, a plurality of configurations can be adopted for the radiating wires 220 by adjusting the shape or by increasing or decreasing the length or width of the wires 220 and the positioning of the wires 220 according to the polarization of the array of antennas of transmission means 110.

Each sensor 200 furthermore includes two feed wires 240 that feed the nonlinear electronic component 230, said feed wires 240 preferably being arranged perpendicular to the direction of polarization of the array of antennas of transmission means 110.

This provides the advantage of decreasing the influence of the feed wires 240 on the incident electromagnetic field.

Moreover, the configuration in which the feed wires 240 and the wires 220 are respectively arranged perpendicularly and at $\alpha=45°$ with respect to the direction of polarization of the array of transmission antennas allows for free use of filtering means along the feed wires 240 and especially along the low pass filter that is intended to block the signals generated at the frequency Fp on the wires while ensuring the passage of the signals at the modulation frequency Fm2.

Furthermore, the substrate 210, on which the collection of the other elements is situated, can be flexible or rigid. It advantageously has dielectric properties as well as a minimal thickness which makes it possible to limit the reflections at the interface and to reduce the losses in amplitude of the incident electromagnetic signal.

In the case of a substrate 210 that is flexible, conformed configurations of the arrays of sensors 200 are possible. For example, an array of sensors 200 of the circular type makes it possible to adapt the control to a material progressing along a tube, for example.

The modulating elements 230 integrated in the sensors 200 are preferably nonlinear electrical components of electrophotonic components.

The feed wires 240 can be printed electrical wiring or unprinted electrical wiring, while in the case of the electrophotonic sensors, the feed wires 240 are replaced by optical fibers or a laser beam.

FIG. 5 depicts an array of sensors identical to the sensor 200 that will be described in relation to FIG. 4.

The length of the array ought to be equal to or greater than the width of the material 150 to be controlled in order to make it possible to entirely control said material.

The sensors 200 of the array are preferably regularly spaced. More specifically, they are spaced at a determined distance D, which make it possible to define the spatial resolution of the device.

Indeed, the smaller the distance D, the smaller the width of the zone of the material 150 analyzed by a sensor 200.

Furthermore, the sensors 200 placed in the array can each have dimensions and angular positions that are different with regard to the polarization of the array of antennas of transmission means 110.

A variant of the embodiment enables arranging the sensors 200 successively with their wires 220 directed at α=+45° and α=−45° with respect to the direction of polarization of the array of antennas of transmission means 110.

This makes it possible to generate a bipolarization for the array of receivers 200 as well as to measure the two components of the incident electromagnetic field.

Yet another variant of the embodiment provides for using an arrangement of a plurality of nonlinear electronic components 230 placed in series by, for example, charging the wires 220 of the sensor.

Furthermore, another variant of the embodiment consists of fragmenting the wires 220 of the sensor that are charged by an arrangement of a plurality of nonlinear electronic components 230.

Moreover, yet another variant of the embodiment allows for stacking two sensors 200 having two angular positions that are different from the polarization of the array of antennas of transmission means 110. This makes it possible to generate a bipolarization of the formed global sensor 200 as well as to measure the two components of the incident electromagnetic field in local coincidence.

Finally, another variant of the embodiment provides for using the antennas of transmission means and/or the bipolarized reception in combinations with the bipolarized sensors in such a manner so as to make it possible to effect polarimetric measurements of the defects in the materials.

The invention claimed is:

1. A device for controlling a material, comprising:
   at least one transmitter for transmitting an electromagnetic signal at a carrier frequency Fp to illuminate said material, and
   at least one receiver for receiving said electromagnetic signal,
   wherein said device further comprises:
   a first modulator for modulating said electromagnetic signal at a frequency Fm1, said modulator being arranged, on signal path, between said transmitter and said material for spatially sampling said emitted electromagnetic signal,
   a second modulator for modulating said electromagnetic signal at a frequency Fm2, said modulator being arranged, on signal path, between said material and the electromagnetic signal receiver for spatially sampling said electromagnetic signal passed through said material, and
   a demultiplexer for demultiplexing said modulating signal toward said second modulator.

2. The device according to claim 1, wherein said first and second modulator include an array of spatial modulation sensors, each of said sensors being formed by a nonlinear electronic component or by an array of nonlinear electronic components fed at the desired modulation frequency Fm and charging two or more radiating wires each connected to said component(s).

3. The device according to claim 2, wherein each of said sensors includes two feed wires feeding the nonlinear electronic component, said feed wires being arranged perpendicular to the direction of polarization of the transmitter.

4. The device according to claim 2, wherein said nonlinear electronic component is an electronic diode, a photoelectric diode or a thermistor and said feed wires can be imprinted or non-imprinted electrical wires or optical fibers.

5. The device according to claim 2, wherein said sensors are electric dipoles charged by the nonlinear elements such as electric diode, photoelectric diode or thermistor type.

6. The device according to claim 2, wherein said sensors of an array are regularly spaced.

7. The device according to claim 6, wherein all sensors of each array, facing the material, are aligned in one or more rows in a common plane perpendicular to propagation direction of said signal transmitted by said transmitter.

8. The device according to claim 6, wherein each sensor includes said radiating wires positioned at ±45° with respect to polarization direction of said transmitter.

9. The device according to claim 1, wherein said transmitter, on one hand, and said second modulator and receiver, on the other hand, are arranged on either side of said material such that said second modulator receives said signal transmitted through said material.

10. The device according to claim 1, wherein said transmitter, on one hand, and said second modulator and receiver, on the other hand, are arranged on the same side with respect to said material such that said modulator receives said signal reflected by said material.

11. The device according to claim 1, wherein said transmitter and said receiver each includes an array of antennas of the same type.

12. The device according to claim 1, wherein said demultiplexer are temporal or spatial demultiplexer.

13. The device according to claim 1, wherein said device further includes a filter for filtering said signals received by said receiver.

14. The device according to claim 2, wherein said sensors include a flexible substrate enabling each sensor array to be formed.

15. A method for controlling a material, comprising the steps of:
   transmitting an electromagnetic signal at a frequency Fp for illuminating said material,
   modulating said transmitted electromagnetic signal at a modulation frequency Fm1 prior its reaching said material,
   modulating and receiving said electromagnetic signal from said material at a modulation frequency Fm2,
   demultiplexing said electromagnetic signal modulated at the frequency Fm2, and
   obtaining an image of said material on the basis of said signal resulting from said steps of modulating.

* * * * *